United States Patent [19]

Berg

[11] Patent Number: 5,738,763
[45] Date of Patent: Apr. 14, 1998

[54] SEPARATION OF 2-METHYL-1-PROPANOL FROM 2-METHYL-1-BUTANOL BY EXTRACTIVE DISTILLATION

[76] Inventor: Lloyd Berg, 1314 S. Third Ave., Bozeman, Mont. 59715

[21] Appl. No.: 676,780

[22] Filed: Jul. 8, 1996

[51] Int. Cl.$^6$ .............................. B01D 3/40; C07C 29/84
[52] U.S. Cl. ............................ 203/57; 203/58; 203/59; 203/60; 203/62; 203/63; 203/67; 203/69; 568/913
[58] Field of Search ....................... 203/57, 58, 60, 203/62, 69, 63, 59, 68, 70, 67; 568/913

[56] References Cited

U.S. PATENT DOCUMENTS

| | | | |
|---|---|---|---|
| 2,559,520 | 7/1951 | Smith, Jr. et al. | 203/64 |
| 4,969,977 | 11/1990 | Berg | 203/60 |
| 5,320,715 | 6/1994 | Berg | 203/57 |
| 5,358,608 | 10/1994 | Berg | 203/62 |
| 5,407,540 | 4/1995 | Berg | 203/58 |
| 5,407,542 | 4/1995 | Berg | 203/63 |
| 5,417,814 | 5/1995 | Berg | 203/60 |
| 5,645,695 | 7/1997 | Berg | 203/57 |

FOREIGN PATENT DOCUMENTS 0047204  3/1982  European Pat. Off. ........... 203/57

*Primary Examiner*—Virginia Manoharan

[57] ABSTRACT

2-Methyl-1-propanol is difficult to separate from 2-methyl-1-butanol by conventional distillation or rectification because of the proximity of their boiling points. 2-Methyl-1-propanol can be readily separated from 2-methyl-1-butanol by extractive distillation. Effective agents are hexyl formate, 2-heptanone and dipropyl amine.

1 Claim, No Drawings

SEPARATION OF 2-METHYL-1-PROPANOL FROM 2-METHYL-1-BUTANOL BY EXTRACTIVE DISTILLATION

FIELD OF THE INVENTION

This invention relates to a method for separating 2-methyl-1-propanol from 2-methyl-1-butanol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

2-Methyl-1-propanol and 2-methyl-1-butanol boil about twenty degrees apart and have a relative volatility of 2.3 and are fairly difficult to separate by conventional rectification. Table 2 shows that to get 99% purity, fifteen actual plates are required. With an agent giving a relative volatility of 3.5, only nine actual plates are required.

TABLE 2

Theoretical and Actual Plates Required vs. Relative Volatility for 2-Methyl-1-propanol-2-Methyl-1-Butanol Separation

| Relative Volatility | Theoretical Plates Required At Total Reflux, 99% Purity | Actual Plates Required, 75% Eff. |
|---|---|---|
| 2.3 | 11 | 15 |
| 3.0 | 8 | 11 |
| 3.5 | 7 | 9 |

OBJECTIVE OF THE INVENTION

The object of this invention is to provide a process or method of extractive distillation that will enhance the relative volatility of 2-methyl-1-propanol to 2-methyl-1-butanol in their separation in a rectification column. It is a further object of this invention to identify effective extractive distillation agents that are stable and can be recycled.

SUMMARY OF THE INVENTION

The objects of this invention are provided by a process for the separation of 2-methyl-1-propanol from 2-methyl-1-butanol which entails the use of certain organic compounds when employed as the agent in extractive distillation.

DETAILED DESCRIPTION OF THE INVENTION

I have discovered that certain organic compounds will effectively increase the relative volatility between 2-methyl-1-propanol and 2-methyl-1-butanol during rectification when employed as the agent in extractive distillation. Table 3 summarizes the data obtained with these agents. The agents which are effective are sulfolane, propyl butyrate, hexyl formate, 2-butoxyethyl acetate, triacetin, di-tert. butyl dicarbonate, butyl lactate, ditridecyl phthalate, n-pentyl propionate, ethyl salicylate, 2-octanone, propiophenone, 2-undecanone, dimethylformamide, anisole, acetonitrile, 1-methyl piperazine, 1,1,3,3-tetramethyl urea, methyl isobutyl ketoxime, methyl ethyl ketoxime, nitroethane, 1-nitropropane, o-xylene, 2-methylamino-2-methyl-1-propanol, p-xylene, 3-carene, d-limonene, 2-picolene, cyclohexyl amine, dipropyl amine, 3-dimethylaminopropyl amine, butyl amine, diisobutyl amine, octane, isoamyl formate, amyl acetate, ethyl phenyl acetate, 2-heptanone, methyl heptanoate, methyl valerate, butyl butyrate, ethyl benzoate, ethyl lactate, Propyl propionate, n-butyl propionate, 1,2,3,4-tetrahydronaphthalene and decalin.

TABLE 3

Effective Extractive Distillation Agents For Separating 2-Methyl-1-propanol From 2-Methyl-1-butanol

| Compounds | Relative Volatility |
|---|---|
| None | 2.3 |
| Sulfolane | 2.5 |
| Propyl butyrate | 2.7 |
| Hexyl Formate | 3.0 |
| 2-Butoxyethyl acetate | 3.0 |
| Di-tert. Butyl dicarbonate | 2.5 |
| Triacetin | 2.7 |
| Butyl lactate | 2.6 |
| Ditridecyl phthalate | 2.5 |
| n-Pentyl propionate | 2.5 |

TABLE 3-continued

Effective Extractive Distillation Agents For
Separating 2-Methyl-1-propanol From 2-Methyl-1-butanol

| Compounds | Relative Volatility |
|---|---|
| Ethyl salicylate | 2.5 |
| 2-Octanone | 2.7 |
| Propiophenone | 2.8 |
| 2-Undecanone | 2.6 |
| Dimethylformamide | 2.5 |
| Anisole | 2.9 |
| Acetonitrile | 2.6 |
| 1,1,3,3-Tetramethyl urea | 3.1 |
| 1-Methyl piperazine | 2.5 |
| Methyl isobutyl ketoxime | 2.9 |
| Methyl ethyl ketoxime | 2.5 |
| Nitroethane | 3.2 |
| 1-Nitropropane | 2.5 |
| 2-Methylamino-2-methyl-1-propanol | 2.6 |
| o-Xylene | 2.7 |
| p-Xylene | 2.7 |
| 3-Carene | 2.6 |
| d-Limonene | 2.6 |
| 2-Picolene | 2.5 |
| Cyclohexyl amine | 3.1 |
| Dipropyl amine | 3.0 |
| 3-Dimethylaminopropyl amine | 2.9 |
| Butyl amine | 2.6 |
| Diisobutyl amine | 2.6 |
| Octane | 2.6 |
| Isoamyl formate | 2.7 |
| Amyl acetate | 2.5 |
| Ethyl phenyl acetate | 2.5 |
| 2-Heptanone | 3.3 |
| Methyl heptanoate | 2.5 |
| Methyl valerate | 2.6 |
| Butyl butyrate | 2.6 |
| Ethyl benzoate | 2.7 |
| Ethyl lactate | 2.6 |
| Propyl propionate | 2.7 |
| n-Butyl propionate | 2.6 |
| 1,2,3,4-Tetrahydronaphthalene | 2.7 |
| Decalin | 2.9 |

THE USEFULNESS OF THE INVENTION

The usefulness or utility of this invention can be demonstrate by referring to the data presented in Tables 1, 2 and 3. All of the successful agents show that 2-methyl-1-propanol can be separated from 2-methyl-1-butanol by means of extractive distillation and that the ease of separation is considerable.

WORKING EXAMPLE

Example 1

Fifty grams of 2-methyl-1-propanol—2-methyl-1-butanol mixture and fifty grams of hexyl formate as the extractive distillation agent were charged to a vapor-liquid equilibrium still and refluxed for two hours. The vapor composition was 81.2% 2-methyl-1-propanol and 18.8% 2-methyl-1-butanol; the liquid composition was 59.4% 2-methyl-1-propanol and 40.6% 2-methyl-1-butanol. This is a relative volatility of 3.0.

I claim:

1. A method for recovering 2-methyl-1-propanol from a mixture of 2-methyl-1-propanol and 2-methyl-1-butanol which consists essentially of distilling a mixture consisting of 2-methyl-1-propanol and 2-methyl-1-butanol in the presence of an extractive distillation agent, recovering the 2-methyl-1-propanol as overhead product and obtaining the 2-methyl-1-butanol and the extractive distillation agent as bottoms product, wherein said extractive distillation agent consists essentially of one material selected from the group consisting of sulfolane, propyl butyrate, hexyl formate, 2-butoxyethyl acetate, triacetin, di-tert.butyl dicarbonate, butyl lactate, ditridecyl phthalate, n-pentyl propionate, ethyl salicylate, 2-octanone, propiophenone, 2-undecanone, dimethylformamide, anisole, acetonitrile, 1-methyl piperazine, 1,1,3,3-tetramethyl urea, methyl isobutyl ketoxime, methyl ethyl ketoxime, nitroethane, 1-nitropropane, o-xylene, 2-methylamino-2-methyl-1-propanol, p-xylene, 3-carene, d-limonene, 2-picolene, cyclohexyl amine, dipropyl amine, 2-dimethylaminopropyl amine, butyl amine, diisobutyl amine, octane, isoamyl formate, amyl acetate, ethyl phenyl acetate, 2-heptanone, methyl heptanoate, methyl valerate, butyl butyrate, ethyl benzoate, ethyl lactate, propyl propionate, n-butyl propionate, 1,2,3,4-tetrahydronaphthalene and decalin.

* * * * *